United States Patent
Sava et al.

(10) Patent No.: US 7,074,965 B2
(45) Date of Patent: Jul. 11, 2006

(54) DIPHOSPHINE

(75) Inventors: Xavier Sava, Mannheim (DE); Michael Slany, Kirchheim (DE); Michael Röper, Wachenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/491,419

(22) PCT Filed: Sep. 26, 2002

(86) PCT No.: PCT/EP02/10798

§ 371 (c)(1),
(2), (4) Date: Apr. 1, 2004

(87) PCT Pub. No.: WO03/031457

PCT Pub. Date: Apr. 17, 2003

(65) Prior Publication Data

US 2004/0249216 A1    Dec. 9, 2004

(30) Foreign Application Priority Data

Oct. 2, 2001   (DE) ................................ 101 48 712

(51) Int. Cl.
*C07F 9/01* (2006.01)
(52) U.S. Cl. ......................................... 568/10; 568/12
(58) Field of Classification Search .................. 568/10, 568/12
See application file for complete search history.

(56) References Cited

FOREIGN PATENT DOCUMENTS

| EP | 273 489 | 7/1988 |
|---|---|---|
| EP | 495 547 | 7/1992 |
| WO | 98/42717 | 10/1998 |
| WO | WO 98/42717 | * 10/1998 |
| WO | 1/87899 | 11/2001 |

* cited by examiner

*Primary Examiner*—Johann Richter
*Assistant Examiner*—Chukwuma Nwaonicha
(74) *Attorney, Agent, or Firm*—Novak, Druce & Quigg, LLP; Jason D. Voight

(57) ABSTRACT

A system comprising a diphosphine of the formula $$R^1{>}P{-}(CH)_n{-}PR^2R^3$$

where
$R^1$ is a divalent radical which together with the phosphorus atom to which it is linked forms an unsubstituted or substituted 2-phosphatricyclo[3.3.1.1{3,7}]decyl group or a derivative thereof in which one or more of the carbon atoms are replaced by heteroatoms,
$R^2$, $R^3$ are each, independently of one another, a monovalent radical having from 1 to 20 atoms or together form a divalent radical having from 2 to 20 atoms,
n is 4 or 5,
and a mixture of such diphosphines,
and palladium or a palladium compound is suitable as carbonylation catalyst for the carbonylation of a conjugated diene.

18 Claims, No Drawings

DIPHOSPHINE

The present invention relates to a diphosphine of the formula

$$R^1 > P-(CH_2)_n-PR^2R^3$$

where $R^1$ is a divalent radical which together with the phosphorus atom to which it is linked forms an unsubstituted or substituted 2-phosphatricyclo[3.3.1.1{3,7}]decyl group or a derivative thereof in which one or more of the carbon atoms are replaced by heteroatoms, $R^2$, $R^3$ are each, independently of one another, a monovalent radical having from 1 to 20 atoms or together form a divalent radical having from 2 to 20 atoms, n is 4 or 5, and mixtures of such diphosphines.

The invention further relates to a system which is suitable as carbonylation catalyst and comprises palladium or a palladium compound and such a diphosphine, and also to a process for the carbonylation of a conjugated diene in the presence of such a system.

Alkenecarboxylic acids and their derivatives are important intermediates in organic synthesis, for example the synthesis of active compounds and polymers. Thus, for example, pentenoic acid or its derivatives, e.g. esters, can be converted by further functionalization into adipic acid derivatives or 6-aminocaproic acid derivatives. Adipic acid and 6-aminocaproic acid are important starting compounds for the preparation of industrially important polymers, in particular polyamides.

Processes for preparing alkenecarboxylic acid derivatives by carbonylation of conjugated dienes in the presence of a hydroxyl-containing compound in the liquid phase in the presence of a system which is suitable as carbonylation catalyst and comprises a palladium compound and a multidentate organic phosphorus ligand are known, for example from EP 273 489 A1 or EP 495 547 A2.

A disadvantage of these processes is that palladium deposits as metal and is thus removed from the catalytically active system. In addition, the metallic palladium is technically difficult to recover from the reaction mixture.

It is known from WO 98/42717 that in the carbonylation of olefins in the presence of catalyst systems comprising palladium or a palladium compound and a multidentate organic phosphorus ligand, the activity can be increased by using a diphosphine of the formula $R^1 > P-R^2-PR^3R^4$ in which $R^1$ is an unsubstituted or substituted 2-phosphatricyclo[3.3.1.1{3,7}]decyl group, $R^2$ is a bridging group, $R^3$ and $R^4$ are each, independently of one another, a monovalent radical having from 1 to 20 carbon atoms or together form a divalent radical having from 2 to 20 carbon atoms as multidentate organic phosphorus ligand. Specific examples mentioned for $R^2$ are only the 1,2-ethane and 1,3-propane groups. According to the examples given in WO 98/42717, such diphosphines appear to lead to high activities or selectivities in the carbonylation of ethylene, proene, alpha-$C_{14}$-olefins and methyl 3-pentenoate. However, if such systems are employed in the case of conjugated dienes such as 1,3-butadiene, the selectivity is drastically worse than in the abovementioned EP 273 489 A1.

It is an object of the present invention to provide a system which is suitable as carbonylation catalyst and comprises a palladium compound and a multidentate organic phosphorus ligand and makes it possible to carry out the carbonylation of a conjugated diene in the presence of a hydroxyl-containing compound in the liquid phase in good yields, with high selectivities, with reduced deposition of palladium and in a technically simple and economical manner.

We have found that this object is achieved by the diphosphine defined at the outset, a system which is suitable as carbonylation catalyst and comprises palladium or a palladium compound and such a disphosphine, and a process for the carbonylation of a conjugated diene in the presence of such a system.

According to the present invention, $R^1$ is a divalent radical which together with the phosphorus atom to which it is linked forms a 2-phosphatricyclo[3.3.1.1{3,7}]decyl group or a derivative thereof in which one or more of the carbon atoms are replaced by heteroatoms. To aid understanding of the present invention, mention may be made of the fact that tricyclo[3.3.1.1{3,7}]decane is the systematic name for a compound which is generally known as "adamantane".

In an advantageous embodiment, $R^1$ together with the phosphorus atom to which it is linked can form an unsubstituted 2-phosphatricyclo[3.3.1.1{3,7}]decyl group.

In an advantageous embodiment, $R^1$ together with the phosphorus atom to which it is linked can form a substituted 2-phosphatricyclo[3.3.1.1{3,7}]decyl group, preferably a 2-phosphatricyclo[3.3.1.1{3,7}]decyl group substituted in one or more of the positions 1, 3, 5 and 7 by a monovalent radical $R^4$. $R^4$ is advantageously a radical having from 1 to 20 atoms, for example methyl, trifluoromethyl, ethoxy, phenyl or 4-dodecylphenyl. In a particularly preferred embodiment, each of the positions 1, 3, 5 and 7 is substituted by radicals $R^4$, preferably identical radicals $R^4$.

In the skeleton of $R^1$, one or more carbon atoms can advantageously be replaced by heteroatoms, in particular by oxygen or sulfur, preferably in the positions 6, 9 and 10.

In a preferred embodiment, $R^1$ together with the phosphorus atom to which it is linked is a 2-phospha-1,3,5,7-tetramethyl-6,9,10-trioxodamantyl group.

According to the present invention, each of the groups $R^2$ and $R^3$ can be, independently of one another, a monovalent radical having from 1 to 20 atoms, e.g. alkyl such as methyl, ethyl, n-propyl, i-propyl, n-butyl, i-butyl, s-butyl, t-butyl, cyclohexyl, aryl such as phenyl, o,o-di(t-butoxy)phenyl, heteroaryl such as pyridyl, unsubstituted or substituted heterohydrocarbyl such as trimethylsilyl or alkoxy such as methoxy, ethoxy, n-propoxy, i-propoxy, n-butoxy, i-butoxy, s-butoxy, t-butoxy.

$R^2$ and $R^3$ may also together form a divalent radical having from 2 to 20 atoms, e.g. 1,5-pentylene, 1,6-hexylene, 1,3-cyclooctylene, 1,4-cyclooctylene. Preference is given to $R^2$ and $R^3$ together with the phosphorus atom to which they are linked together forming a 2-phosphatricyclo[3.3.1.1{3,7}]decyl group, with the embodiments described above for $R^1$. In a particularly preferred embodiment, $R^2$ and $R^3$ together form a group identical to $R^1$.

According to the present invention, n is 4 or 5.

In a preferred embodiment, n is 4.

In another preferred embodiment, n is 5.

Particularly preferred diphosphines are diphosphines selected from the group consisting of 1,4-P,P'-di(2-phospha-1,3,5,7-tetramethyl-6,9,10-trioxatricyclo[3.3.1.1{3,7}]decyl)butane, 1,4-P,P'-diperfluoro(2-phospha-1,3,5,7-tetramethyl-6,9,10-trioxatricyclo[3.3.1.1{3,7}]decyl)butane, 1,4-P,P'-di(2-phospha-1,3,5,7-tetra(trifluoromethyl)-6,9,10-trioxatricyclo[3.3.1.1{3,7}]decyl)butane, preferably 1,4-P,P'-di(2-phospha-1,3,5,7-tetramethyl-6,9,10-trioxatricyclo[3.3.1.1{3,7}]decyl)butane.

Further particularly preferred diphosphines are diphosphines selected from the group consisting of 1,5-P,P'-di(2- phospha-1,3,5,7-tetramethyl-6,9,10-trioxatricyclo[3.3.1.1{3,7}]decyl)pentane, 1,5-P,P'-diperfluoro(2-phospha-1,3,5,7-tetramethyl-6,9,10-trioxatricyclo[3.3.1.1{3,7}]decyl)pentane, 1,5-P,P'-di(2-phospha-1,3,5,7-tetra(trifluoromethyl)-6,9,10-trioxatricyclo[3.3.1.1{3,7}]decyl)pentane, preferably 1,5-P,P'-di(2-phospha-1,3,5,7-tetramethyl-6,9,10-trioxatricyclo[3.3.1.1{3,7}]decyl)pentane.

The preparation can be carried out in a manner similar to the process described in WO 98/42717, for example for 1,2-P,P'-di(2-phospha-1,3,5,7-tetramethyl-6,9,10-trioxatricyclo[3.3.1.1{3,7}]decyl)ethane or 1,3-P,P'-di(2-phospha-1,3,5,7-tetramethyl-6,9,10-trioxatricyclo[3.3.1.1{3,7}]decyl)propane. Thus, for example, 1,4-P,P'-di(2-phospha-1,3,5,7-tetramethyl-6,9,10-trioxatricyclo[3.3.1.1{3,7}]decyl)butane can be obtained by reacting 2,4-pentanedione with 1,4-diphosphinobutane or 1,5-P,P'-di(2-phospha-1,3,5,7-tetramethyl-6,9,10-trioxatricyclo[3.3.1.1{3,7}]decyl)pentane can be obtained by reacting 2,4-pentanedione with 1,5-diphosphinopentane. Unsymmetrical diphosphines can be prepared, for example, by reaction of a 1,4-diphosphinobutane or 1,5-diphosphinopentane having one primary phosphino group and one tertiary phosphino group. Alternatively, they can be prepared by reaction of a secondary 2-phosphatricyclo[3.3.1.1{3,7}]decane with another secondary monophosphine or by other known methods. Substituted diphosphines can be prepared, for example, by using substituted 2,4-pentanediones, e.g. perfluoro-2,4-pentanedione or 1,1,1,5,5,5-hexafluoro-2,4-pentanedione, in the reaction with 1,4-diphosphinobutane or 1,5-diphosphinopentane.

According to the present invention, the system which is suitable as carbonylation catalyst comprises (I) palladium or a palladium compound and
(II) one of the above-described diphosphines.

The component (II) can be a particular diphosphine of the present invention or a mixture of such diphosphines.

It is likewise possible to use a particular diphosphine of the present invention together with another diphosphine or a mixture of such other diphosphines, or to use a mixture of diphosphines of the present invention together with another diphosphine or a mixture of such other diphosphines.

For the purposes of the present invention, the term "diphosphine" is used both for a particular diphosphine and for a mixture of diphosphines.

The system of the present invention can be used as carbonylation catalyst as described, for example, in EP 273 489 A1, EP 495 547 A2 or WO 98/42717, particularly in the various reactions in which carbon monoxide is added onto an unsaturated compound, preferably onto an olefinic double bond. Such reactions can be schematically represented by

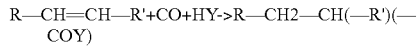

where
Y is H, OH, OR''', NR'''R'''', and
R, R', R'', R''', R'''' are each an organic radical.

The system of the present invention can accordingly be used, for example, in hydroformylation reactions, hydrocarboxylation reactions, hydroesterification reactions, hydroamidation reactions. The system of the present invention has been found to be particularly advantageous in hydrocarboxylation reactions and hydroesterification reactions.

Advantageous unsaturated compounds are conjugated dienes, i.e. organic compounds comprising the structure

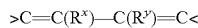

where $R^x$, $R^y$ are each a monovalent radical,
in particular noncyclic compounds such as 1,3-butadiene, 2-methyl-1,3-butadiene, 1,3-pentadiene, 1,3-hexadiene, 2,4-hexadiene, 2,3-dimethyl-1,3-butadiene, preferably 1,3-butadiene.

In the unsaturated compounds, preferably conjugated dienes, one or more hydrogen atoms may be replaced by other atoms, e.g. halogen atoms, or groups of atoms, e.g. hydroxyl groups, cyano groups, methoxy or ethoxy groups, amino groups such as dimethylamino or diethylamino groups, carboxyl groups or ester groups.

In a particularly preferred embodiment, such conjugated dienes can be hydrocarboxylated to give alkenecarboxylic acids, for example pentenoic acids such as cis-2-pentenoic acid, trans-2-pentenoic acid, cis-3-pentenoic acid, trans-3-pentenoic acid, and 4-pentenoic acid from 1,3-butadiene.

In another particularly preferred embodiment, such conjugated dienes can be hydroesterified to give alkenecarboxylic esters, for example pentenoic esters such as cis-2-pentenoic esters, trans-2-pentenoic esters, cis-3-pentenoic esters, trans-3-pentenoic esters and 4-pentenoic esters from 1,3-butadiene.

In such carbonylation reactions, further components such as coreactants or liquid diluents can be used. Likewise, anions can be used as counterion to the palladium cation used in the case of palladium compounds. Examples include anions which are the conjugate base of an acid having a pKa measured in water at 18° C. of less than 6, preferably less than 4. Such anions do not coordinate or coordinate only weakly to palladium, i.e. so that there is no interaction or only a weak interaction between the anion and the palladium cation. Catalysts containing such an anion generally display a good activity.

Suitable anions include anions derived from Brönstedt acids such as phosphoric acid or sulfuric acid, preferably from carboxylic acids, halogenated carboxylic acids or sulfonic acids such as methanesulfonic acid, trifluoromethanesulfonic acid or p-toluenesulfonic acid. Preference is given to anions derived from carboxylic acids, e.g. 2,6-dichlorobenzoic acid, 2,6-dimethoxybenzoic acid and 2,4,6-trimethylbenzoic acid.

It is likewise possible to use complex anions, for example anions obtained from the combination of a Lewis acid, e.g. $BF_3$, $B(C_6F_5)_3$, $AlCl_3$, $SnF_2$, $Sn(CF_3SO_3)_2$, $SnCl_2$ or $GeCl_2$, with a protic acid, preferably a protic acid having a pKa of less than 5, e.g. a sulfonic acid such as $CF_3SO_3H$, $CH_3SO_3H$ or a hydrohalic acid such as HF, HCl, or the combination of a Lewis acid with an alcohol. Examples of such complex anions are $BF_4^-$, $SnCl_3^-$, $[SnCl_2 \cdot CF_3SO_3]^-$ and $PF_6^-$.

The carbonylations can advantageously be carried out at from 30 to 200° C., preferably from 50 to 180° C. The pressure can vary within a wide range. The pressure can advantageously be in a range from 1 to 200 bar, in particular in the range from 5 to 90 bar. Particular preference is given to a pressure which results in the carbonylation taking place in the liquid phase.

Carbon monoxide can advantageously be used in a molar excess over "HY".

The compound "HY" can advantageously be used in a molar ratio to the unsaturated compound of from 10:1 to 1:10, preferably from 5:1 to 1:5, in particular from 2:1 to 1:2.

The amount of catalyst is not critical per se and can vary within a wide range. In general, an amount in the range from $10^{-8}$ to $10^{-1}$ mol, preferably from $10^{-7}$ to $10^{-2}$ mol, of palladium per mol of unsaturated compound has been found to be advantageous.

In the preparation of the system of the present invention, the molar amount of component (II) can generally be somewhat higher than the molar amount of palladium or palladium cation.

A molar ratio of ligand to palladium in the range from 0.5 to 10 has been found to be particularly advantageous.

In the case of particularly active systems, use of diphosphine and palladium in equimolar amounts is possible.

The molar ratio of ligand to palladium is advantageously in the range from 1 to 3, preferably from 1 to 2.

If oxygen is present, a slightly larger amount can be advantageous.

The amount of anion source can advantageously be in the range from 0.5 to 200 mol, preferably from 1 to 80 mol, per mol of palladium.

In the process of the present invention, starting material and product of the carbonylation reaction can act as liquid diluent. In such a case, the use of a further liquid diluent may be able to be dispensed with. It may be advantageous to use a further liquid diluent such as a hydrocarbon, for example an alkane such as a branched or unbranched alkane, or an ether such as 2,5,8-trioxanonane (diglyme), diethyl ether, diphenyl ether or anisole, a sulfone such as sulfolane, or an aromatic hydrocarbon such as toluene.

Suitable coreactants in the carbonylation include compounds having a nucleophilic center and a mobile hydrogen atom.

Preferred nucleophilic compounds are molcular hydrogen, water, alcohols such as monoalcohols, for example, methanol, ethanol, i-propanol, n-propanol, 1-n-butanol, s-butanol, t-butanol, i-butanol, polyalcohols such as ethylene glycol, 1,2-propanediol, 1,3-propanediol, 1,4-butanediol, glycerol, thiols, primary and secondary amines, polyamines, amides and polyamides, for example diethylamine, N,N-dimethylethylenediamine, aromatic alcohols, carboxylic acids such as acetic acid, pivalic acid and propionic acid, in particular molcular hydrogen, monoalcohols having from 1 to 6 carbon atoms, dialcohols having from 2 to 6 carbon atoms, particularly preferably monoalcohols having from 1 to 6 carbon atoms, e.g. methanol, ethanol, i-propanol, n-propanol, 1-n-butanol, s-butanol, t-butanol, i-butanol.

The use of such monoalcohols makes it possible to prepare valuable intermediates such as methyl cis-2-pentenoate, methyl trans-2-pentenoate, methyl cis-3-pentenoate, methyl trans-3-pentenoate, methyl 4-pentenoate. These intermediates can be used, for example, as mentioned above in the preparation of polymers, in particular polyamide 6 and polyamide 66.

Another group of preferred coreactants encompasses alkylphenols, in which one or more of the alkyl groups linked to the phenol part preferably contain(s) up to 30 carbon atoms, preferably from 6 to 22 carbon atoms. The carbonylation described leads in this case to alkylphenyl esters which can be employed as synthetic lubricants, for example in industrial applications or in the automobile sector.

The invention is illustrated by the nonlimiting examples below.

EXAMPLES

Example 1

107 g of diphenyl ether, 20 ml of methanol, 20 ml of butadiene, 0.5 mmol of palladium acetate, 1 mmol of 1,4-P,P'-di(2-phospha-1,3,5,7-tetramethyl-6,9,10-trioxatricyclo[3.3.1.1{3,7}]decyl)butane and 30 mmol of 2,4,6-trimethylbenzoic acid were placed under a nitrogen atmosphere in a 270 ml autoclave fitted with a magnetic stirrer. The autoclave was closed, pressurized with 40 bar of carbon monoxide and heated to 150° C. After this temperature had been reached, the pressure was kept constant for 10 hours by introduction of further carbon monoxide. After the autoclave had been cooled and vented, the reaction solution was taken out. This was a clear yellow solution without a palladium precipitate. The conversion and selectivity to the various products was measured by GC analysis of the solution.

The conversion of butadiene was 82%, and the selectivity to methyl pentenoate was 80.5%.

Comparative Example A

Example 1 was repeated using 1 mmol of 1,3-P,P'-di(2-phospha-1,3,5,7-tetramethyl-6,9,10-trioxatricyclo[3.3.1.1{3,7}]decyl)propane instead of 1 mmol of 1,4-P,P'-di(2-phospha-1,3,5,7-tetramethyl-6,9,10-trioxatricyclo[3.3.1.1{3,7}]decyl)butane. The reaction solution was clear yellow without a palladium precipitate.

The conversion of butadiene was 81%, and the selectivity to methyl pentenoate was 22.8%.

Comparative Example B

Example 1 was repeated using 1 mmol of 1,4-bis(diphenylphosphino)butane in place of 1 mmol of 1,4-P,P'-di(2-phospha-1,3,5,7-tetramethyl-6,9,10-trioxatricyclo[3.3.1.1{3,7}]decyl)butane. After the reaction, the reaction mixture contained a black palladium precipitate. The conversion of butadiene was 97%, and the selectivity to methyl pentenoate was 68.8%.

Comparative Example C

Example 1 was repeated using 1 mmol of 1,3-bis(dicyclohexylphosphino)ethane in place of 1 mmol of 1,4-P,P'-di(2-phospha-1,3,5,7-tetramethyl-6,9,10-trioxatricyclo[3.3.1.1{3,7}]decyl)butane and using 5 mmol of 2,4,6-trimethylbenzoic acid instead of 30 mmol. The reaction solution after the reaction was clear yellow without a palladium precipitate.

The conversion of butadiene was 55%, and the selectivity to methyl pentenoate was 8.9%.

Comparative Example D

Example 1 was repeated using 1 mmol of 1,3-bis(1,5-cyclooctylenephosphino)propane in place of 1 mmol of 1,4-P,P'-di(2-phospha-1,3,5,7-tetramethyl-6,9,10-trioxatricyclo[3.3.1.1{3,7}]decyl)butane. After the reaction, the reaction mixture contained a black palladium precipitate.

The conversion of butadiene was 73%, and the selectivity to methyl pentenoate was 64.5%.

We claim:
1. A diphosphine of the formula

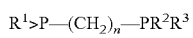

where
$R^1$ is a divalent radical which together with the phosphorus atom to which it is linked forms an unsubstituted or substituted 2-phosphatricyclo[3.3.1.1{3,7}]decyl group or a derivative thereof in which one or more of the carbon atoms are replaced by heteroatoms, $R^2$, $R^3$ are each, independently of one another, a monovalent radical having from 1 to 20 carbon atoms or together form a divalent radical having from 2 to 20 carbon atoms, n is 4 or 5, or a mixture of such diphosphines.

2. A diphosphine as claimed in claim 1, wherein $R^1$ is substituted in one or more of the positions 1, 3, 5 and 7 by a monovalent radical $R^4$ having from 1 to 20 carbon atoms.

3. A diphosphine as claimed in claim 2, wherein $R^4$ is a radical selected from the group consisting of methyl, trifluoromethyl, ethoxy, phenyl and 4-dodecylphenyl.

4. A diphosphine as claimed in claim 1, wherein $R^1$ is substituted in each of the positions 1, 3, 5, and 7 by monovalent radicals $R^4$ having from 1 to 20 carbon atoms.

5. A diphosphine as claimed in claim 1, wherein $R^1$ contains oxygen or sulfur in the skeleton.

6. A diphosphine as claimed in claim 1, wherein $R^1$ is a 2-phospha-1,3,5,7-tetramethyl-6,9,10-trioxaadamantyl group.

7. A diphosphine as claimed in claim 1, wherein $R^2$ and $R^3$ together form a group $R^1$.

8. A diphosphine as claimed in claim 1 in which n is 4.

9. A diphosphine as claimed in claim 1 in which n is 5.

10. A diphosphine as claimed in claim 1 selected from the group consisting of 1,4-P,P'-di(2-phospha-1,3,5,7-tetramethyl-6,9,10-trioxatricyclo[3.3.1.1{3,7}]decyl)butane, 1,4-P,P'-diperfluoro(2-phospha-1,3,5,7-tetramethyl-6,9,10-trioxatricyclo[3.3.1.1{3,7}]decyl)butane, 1,4-P,P'-di(2-phospha-1,3,5,7-tetra(trifluoromethyl)-6,9,10-trioxatricyclo[3.3.1.1{3,7}]decyl)butane.

11. A diphosphine as claimed in claim 1 selected from the group consisting of 1,5-P,P'-di(2-phospha-1,3,5,7-tetramethyl-6,9,10-trioxatricyclo[3.3.1.1{3,7}]decyl)pentane, 1,5-P,P'-diperfluoro(2-phospha-1,3,5,7-tetramethyl-6,9,10-trioxatricyclo[3.3.1.1{3,7}]decyl)pentane, 1,5-P,P'-di(2-phospha-1,3,5,7-tetra(trifluoromethyl)-6,9,10-trioxatricyclo[3.3.1.1{3,7}]decyl)pentane.

12. A composition which is suitable as carbonylation catalyst and comprises (I) palladium or a palladium compound and (II) a diphosphine as claimed in claim 1.

13. A process for preparing an alkenecarboxylic acid or a derivative hereof by carbonylation of a conjugated diene in the presence of a hydroxyl-containing compound in the liquid phase, wherein the carbonylation is carried out in the presence of a system which is suitable as carbonylation catalyst and comprises (I) palladium or a palladium compound and (II) a diphosphine as claimed in claim 1.

14. A process as claimed in claim 13, wherein 1,3-butadiene is used as conjugated diene to give pentenoic acid or a derivative thereof.

15. A diphosphine as claimed in claim 7, wherein the radical represented by $R^2$ and $R^3$ and the radical represented by $R^1$ are identical.

16. A diphosphine as claimed in claim 4, wherein $R^4$ is a radical selected from the group consisting of methyl, trifluoromethyl, ethoxy, phenyl and 4-dodecylphenyl.

17. A diphosphine as claimed in claim 4, wherein the radicals $R^4$ are identical.

18. A diphosphine as claimed in claim 5, wherein the oxygen or sulfur is in 6-, 9- and/or 10-position of $R^1$.

\* \* \* \* \*